(12) United States Patent
Kirschman

(10) Patent No.: US 8,142,436 B2
(45) Date of Patent: Mar. 27, 2012

(54) RETRACTION TUBE FOR USE WITH BONE SCREW

(75) Inventor: David Louis Kirschman, Dayton, OH (US)

(73) Assignee: X-spine Systems, Inc., Miamisburg, OH (US)

(*) Notice: Subject to any disclaimer, the term of this patent is extended or adjusted under 35 U.S.C. 154(b) by 238 days.

(21) Appl. No.: 12/477,489

(22) Filed: Jun. 3, 2009

(65) Prior Publication Data
US 2009/0306721 A1  Dec. 10, 2009

Related U.S. Application Data

(60) Provisional application No. 61/059,417, filed on Jun. 6, 2008.

(51) Int. Cl.
*A61B 17/70* (2006.01)

(52) U.S. Cl. ............................. 606/86 A; 606/104

(58) Field of Classification Search ............... 606/86 A, 606/103–104, 99, 279
See application file for complete search history.

(56) References Cited

U.S. PATENT DOCUMENTS

| | | | |
|---|---|---|---|
| 7,604,655 B2 | 10/2009 | Warnick | |
| 7,662,172 B2 | 2/2010 | Warnick | |
| 7,717,943 B2 | 5/2010 | Kirschman | |
| 2004/0073216 A1* | 4/2004 | Lieberman | 606/61 |
| 2004/0147937 A1 | 7/2004 | Dunbar, Jr. et al. | |
| 2004/0172022 A1* | 9/2004 | Landry et al. | 606/61 |
| 2005/0192579 A1* | 9/2005 | Jackson | 606/72 |
| 2006/0111712 A1 | 5/2006 | Jackson | |
| 2006/0155278 A1 | 7/2006 | Warnick | |
| 2006/0184178 A1* | 8/2006 | Jackson | 606/99 |
| 2007/0032162 A1 | 2/2007 | Jackson | |
| 2007/0043357 A1 | 2/2007 | Kirschman | |
| 2007/0078460 A1 | 4/2007 | Frigg et al. | |
| 2007/0093827 A1 | 4/2007 | Warnick | |
| 2007/0123862 A1 | 5/2007 | Warnick | |
| 2007/0123867 A1 | 5/2007 | Kirschman | |
| 2008/0071277 A1 | 3/2008 | Warnick | |
| 2008/0091213 A1 | 4/2008 | Jackson | |
| 2008/0097457 A1 | 4/2008 | Warnick | |
| 2008/0249576 A1 | 10/2008 | Hawkes et al. | |

FOREIGN PATENT DOCUMENTS

WO 2007025132 A2  3/2007
WO 2008024937 A2  2/2008

* cited by examiner

*Primary Examiner* — Eduardo C Robert
*Assistant Examiner* — Jacqueline Johanas
(74) *Attorney, Agent, or Firm* — Jacox, Meckstroth & Jenkins

(57) ABSTRACT

A retractor system and method for locating and placing a polyaxial screw while substantially simultaneously retracting tissue is shown and described. The retractor has a channel that facilitates introducing a rod into the polyaxial screw. Various embodiments are shown, including one which utilized a reducer for moving the rod in the retractor.

52 Claims, 10 Drawing Sheets

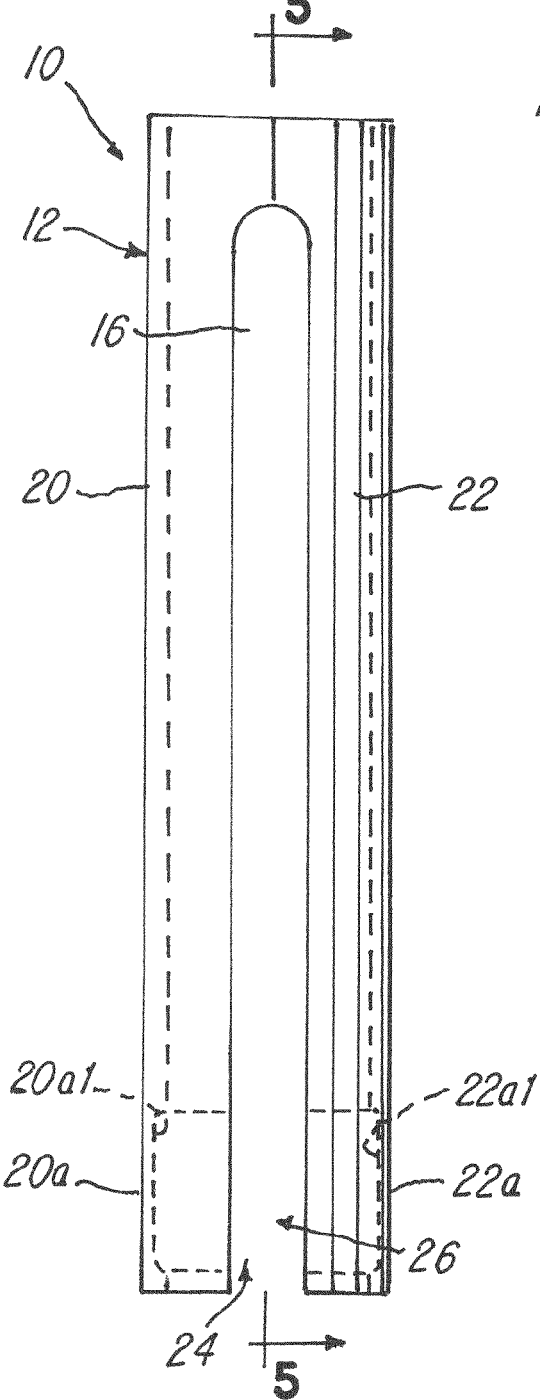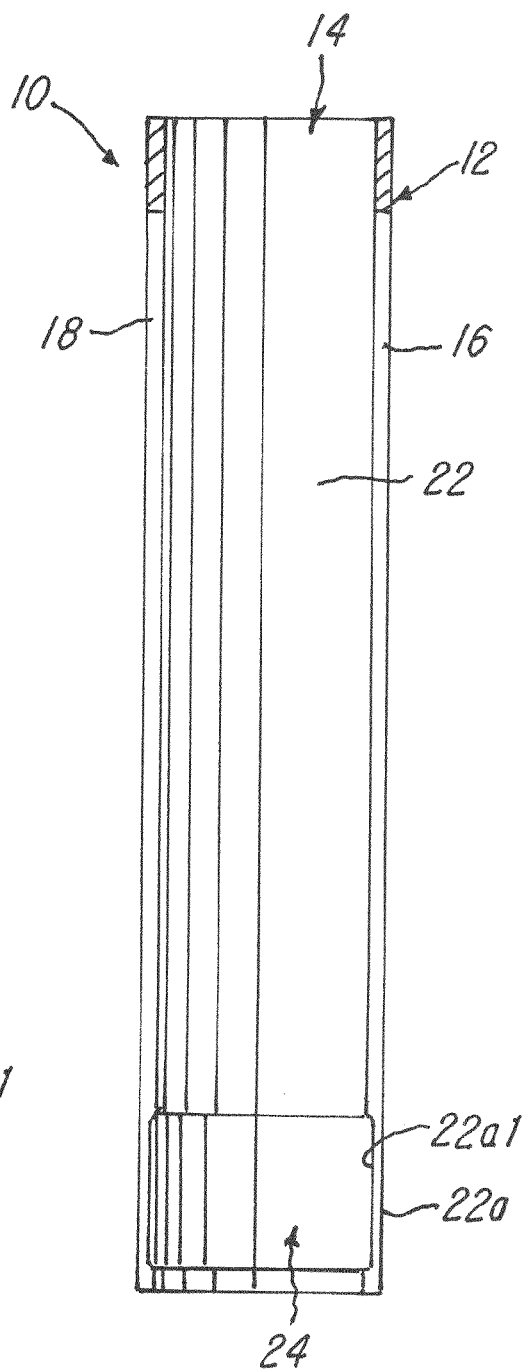

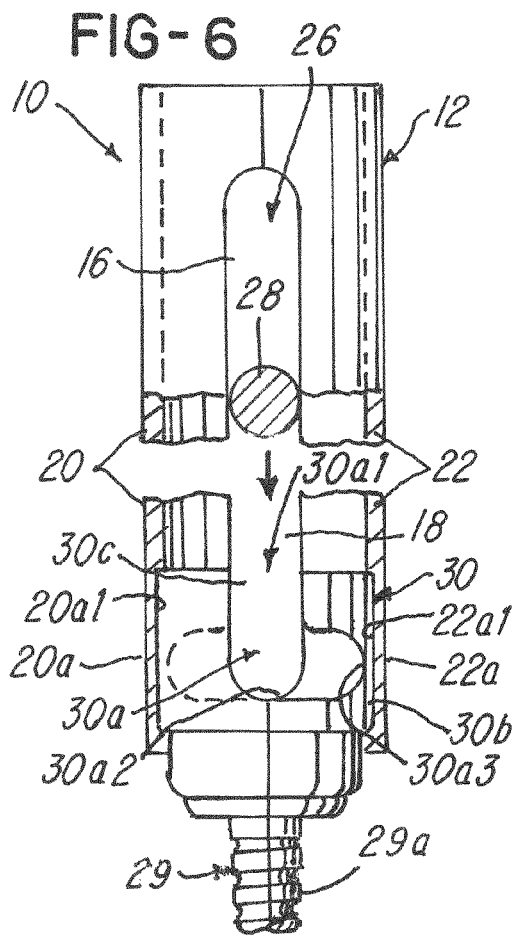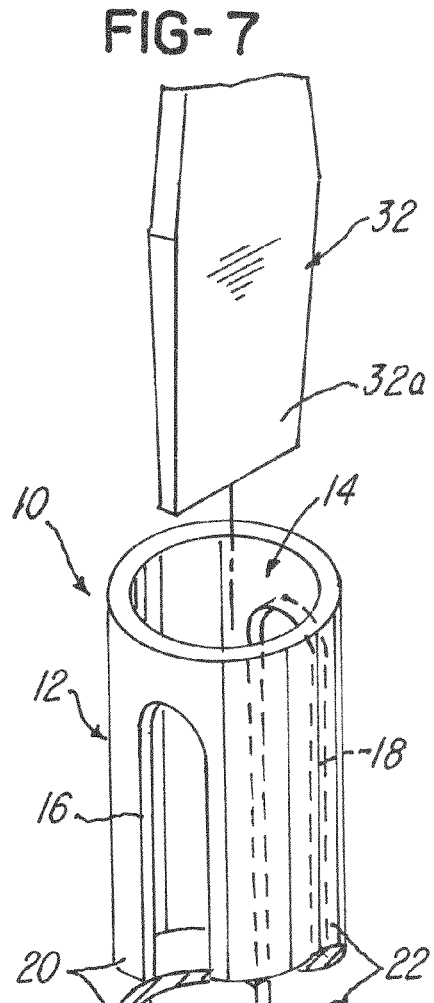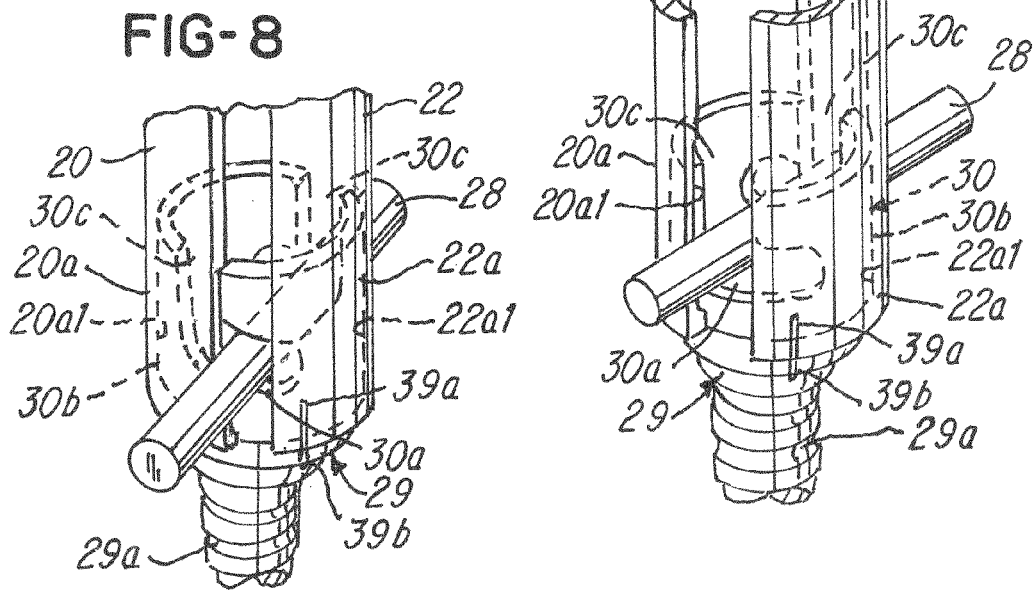

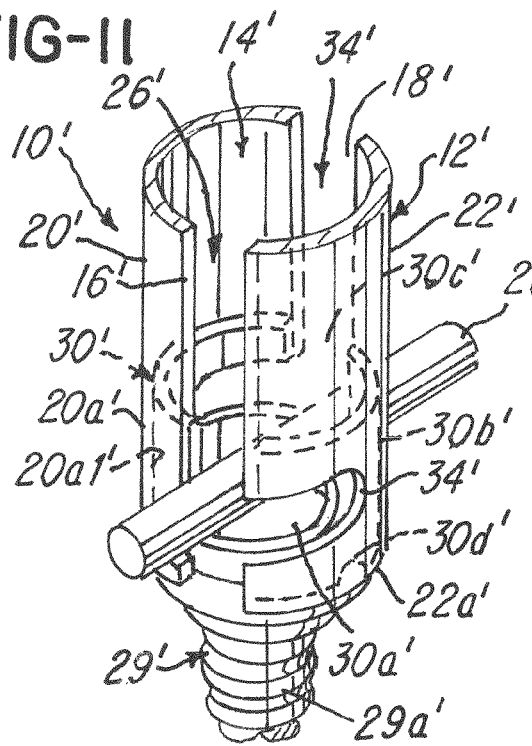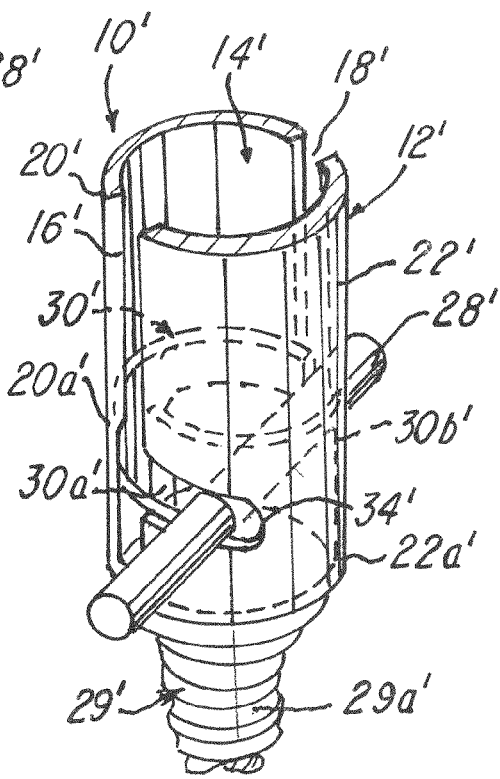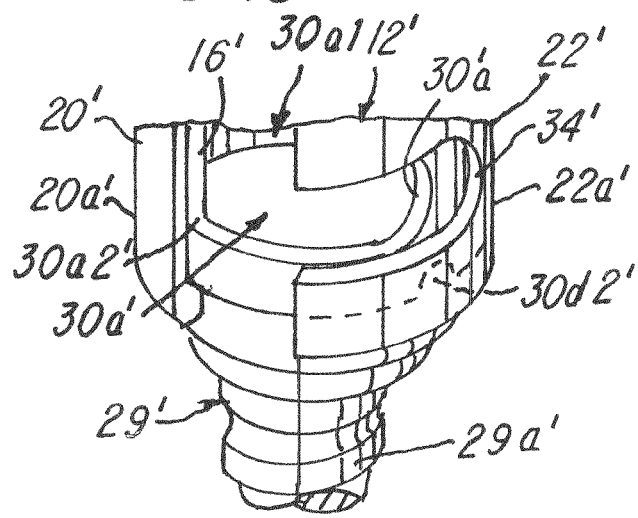

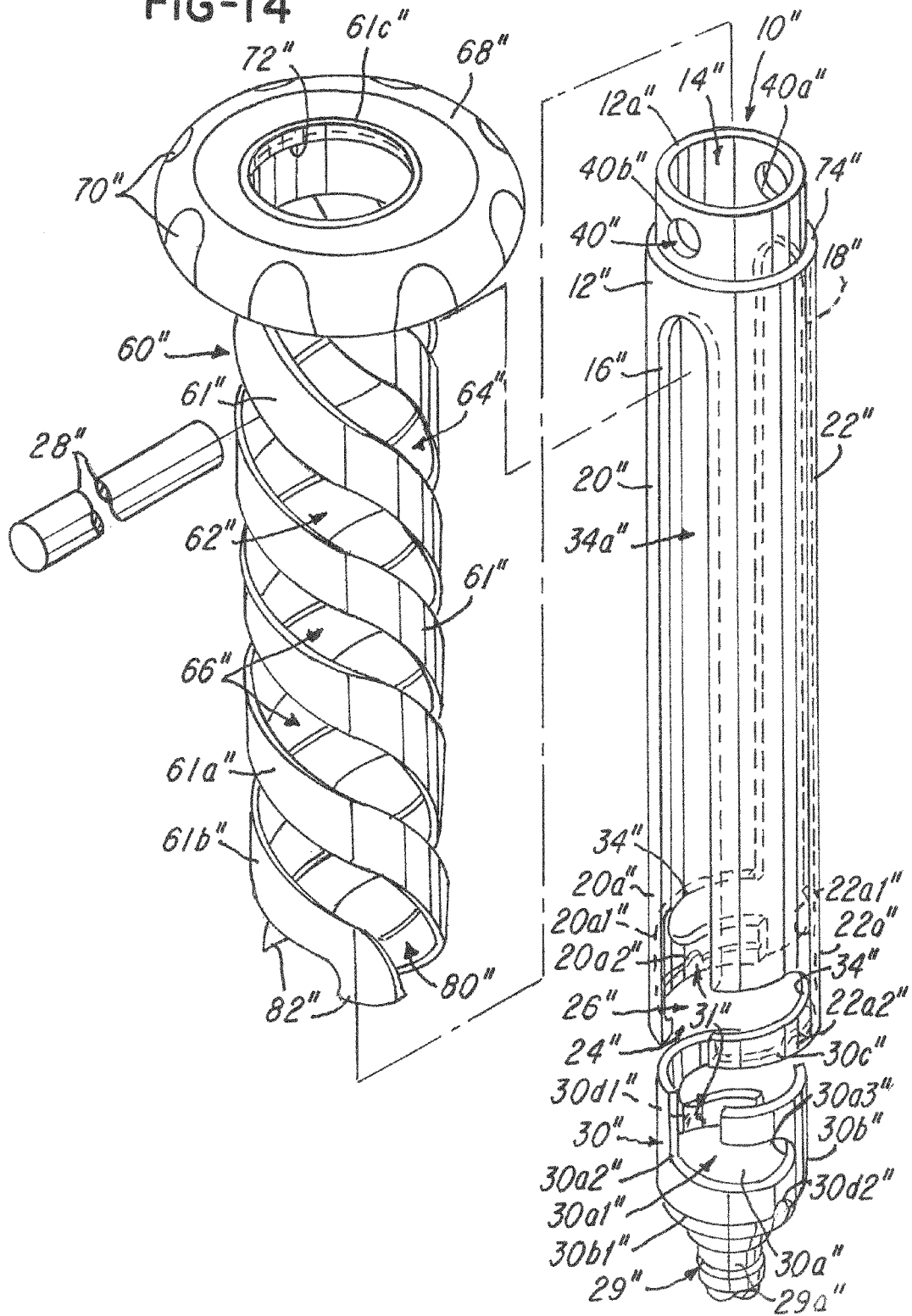

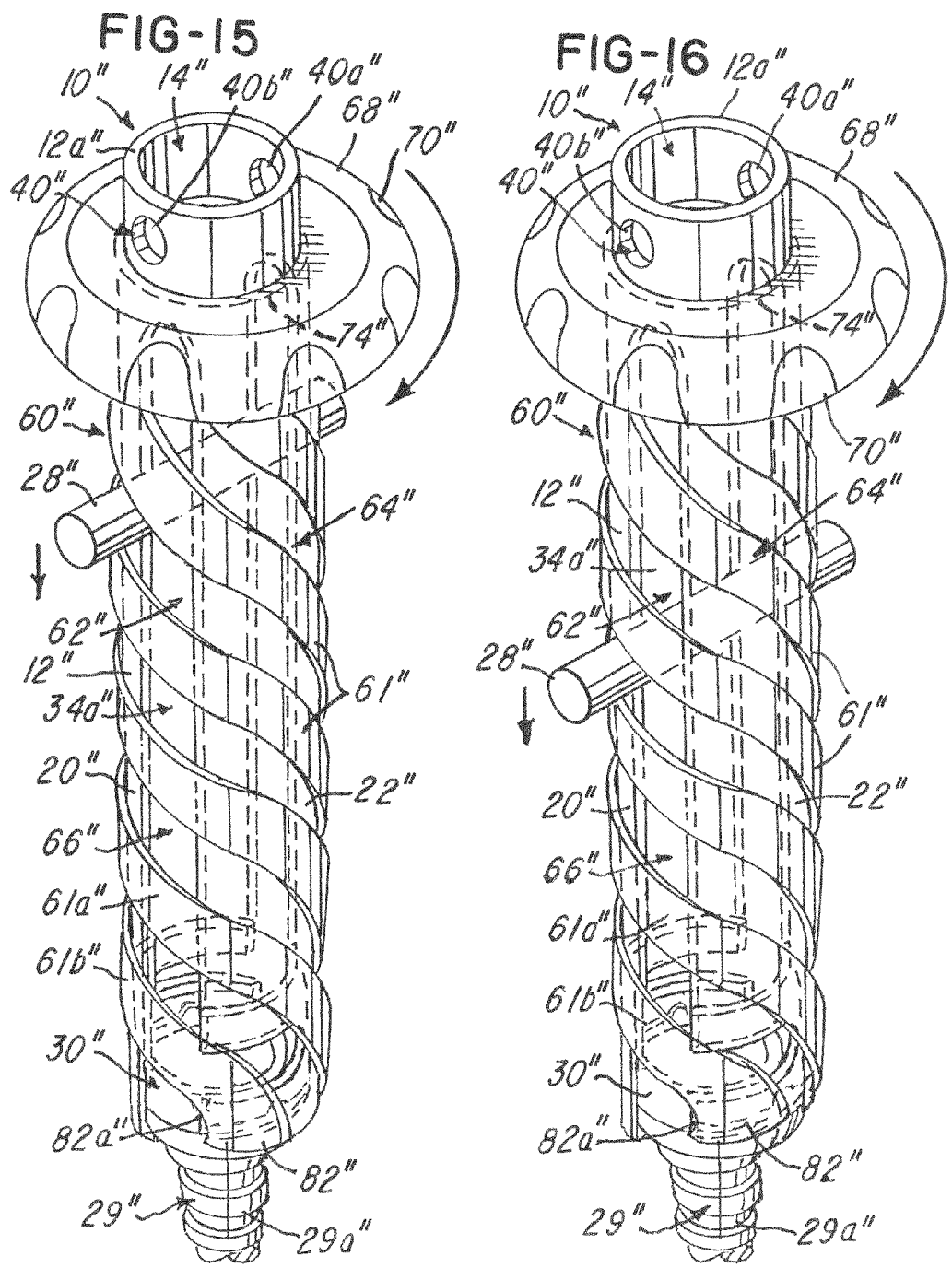

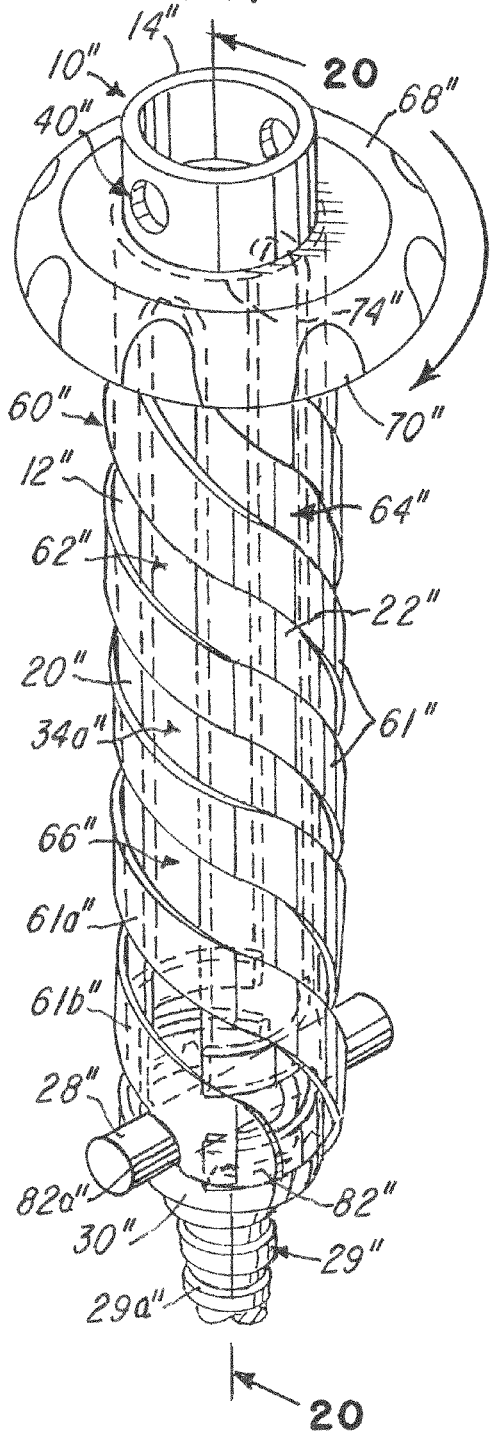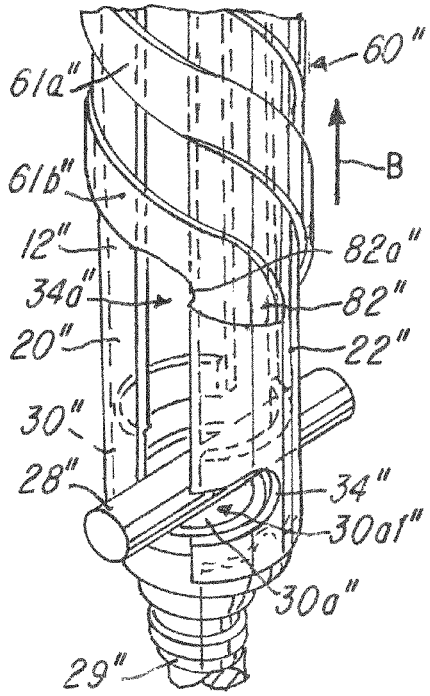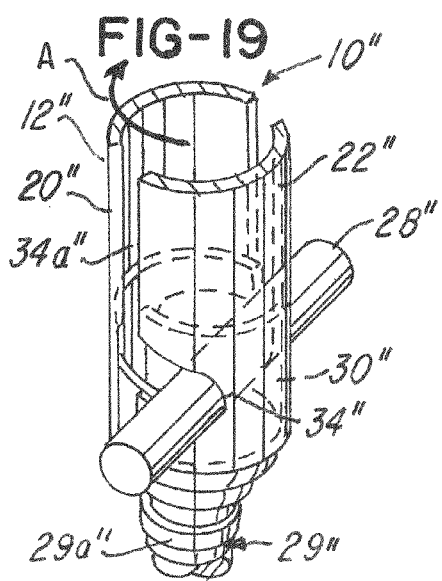

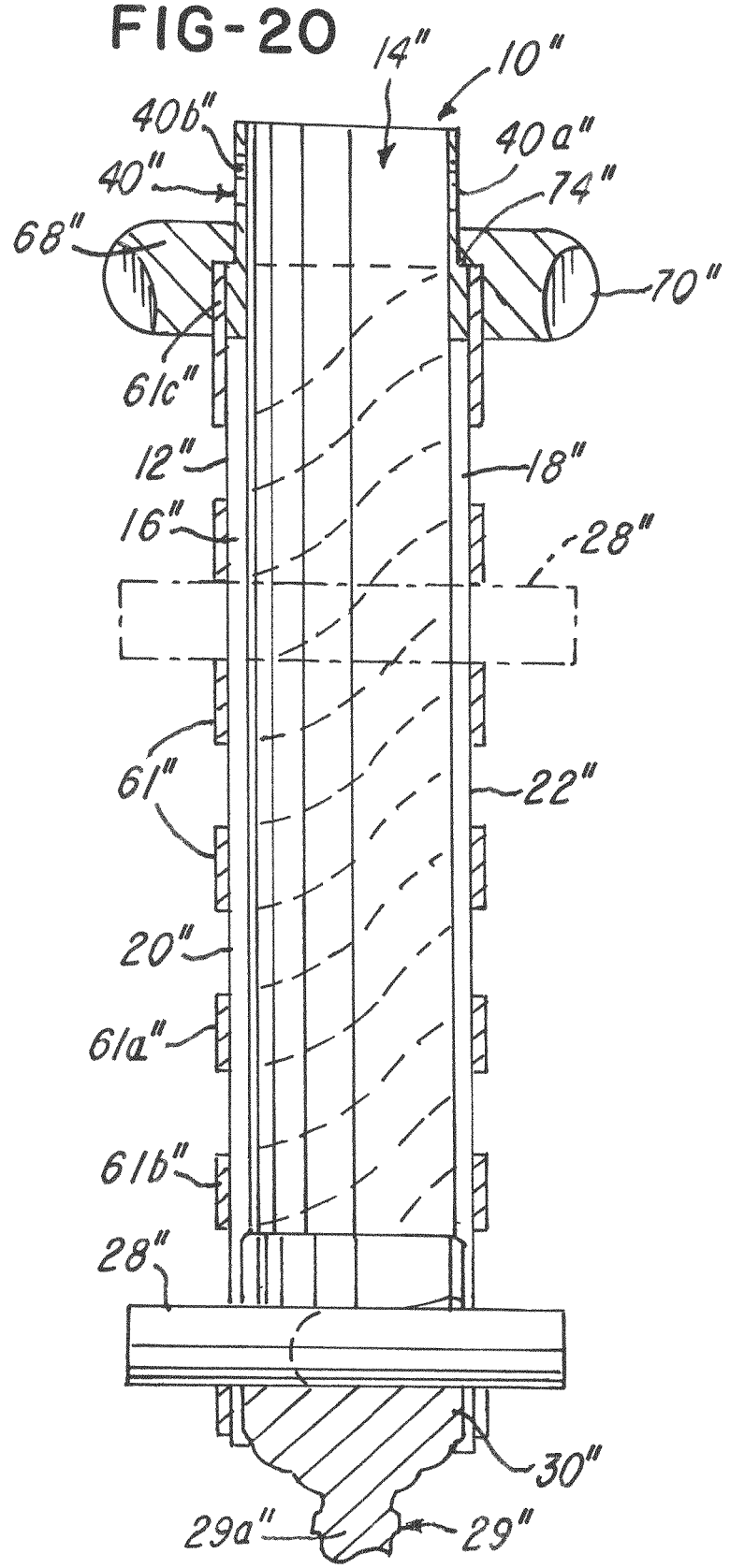

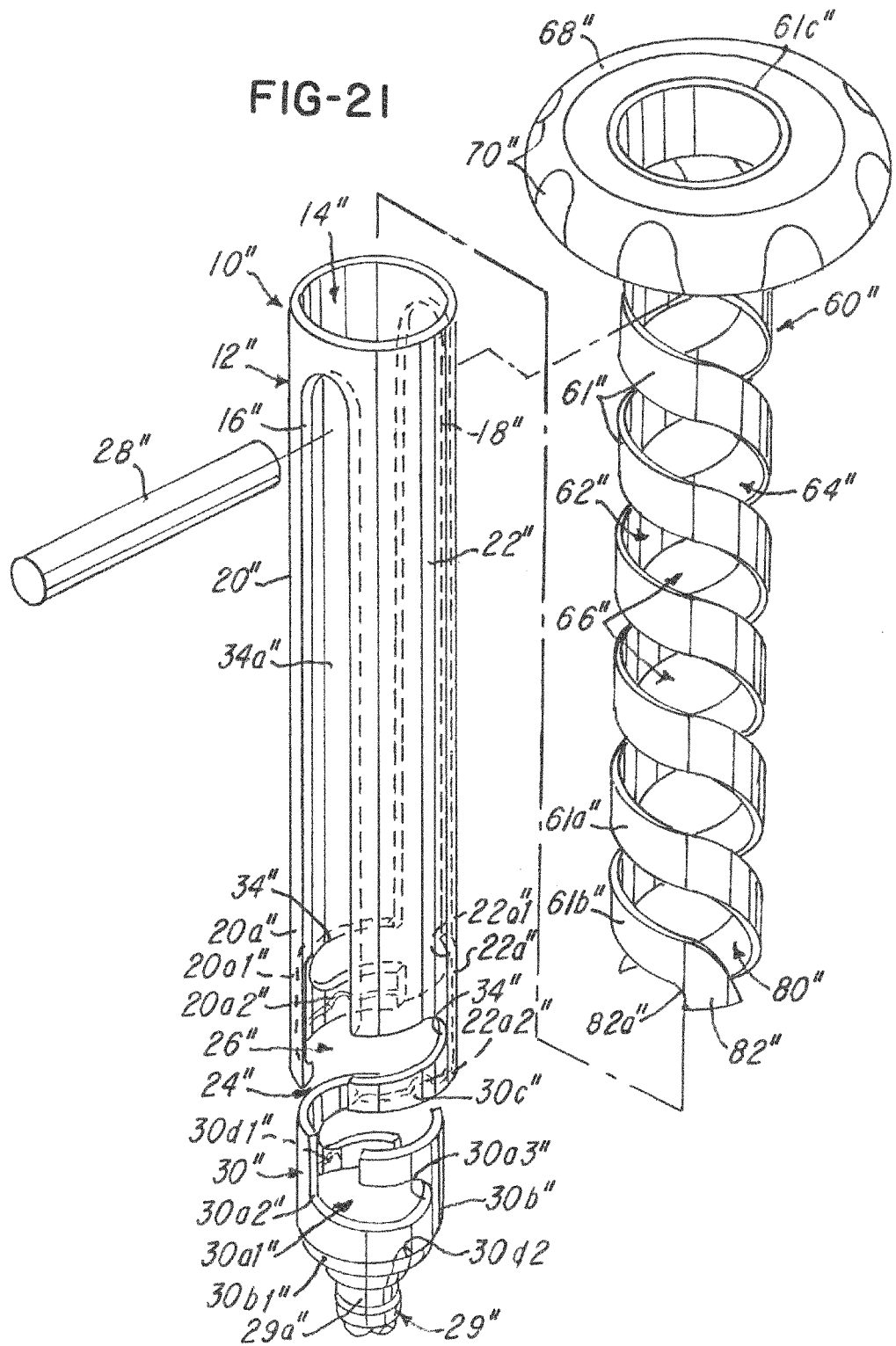

RETRACTION TUBE FOR USE WITH BONE SCREW

CROSS-REFERENCE TO RELATED APPLICATION

The present application claims priority to provisional U.S. Application Ser. No. 61/059,417, filed Jun. 6, 2008, to which Applicant claims the benefit of the earlier filing date. This application is incorporated herein by reference and made a part hereof.

BACKGROUND OF THE INVENTION

1. Field of the Invention

A retraction tube for use with a capless spinal screw which allows for the rotation of the screw locking body within, and relative to, the retraction tube. In another embodiment, a retraction tube for use with a capless spinal screw which attaches rigidly to said screw and is dimensioned to permit rotation of said tubular attachment relative to a fixation element.

2. Description of the Related Art

The placement of spinal screws is a common surgical procedure. There is a need to reduce the size of the incision necessary for the placement of such screws. Small tubular tissue retractors have been used to minimize incision size. More recently, tubular attachments have been developed which attach to the screws themselves, performing tissue retraction during the act of screw placement. Typically, the screws are engaged into bone, while the retraction tubes protrude upward through the skin. At this point a fixation element, typically a metallic rod, is placed either through or adjacent to the retraction tubes in order to engage the screws. Typically, a locking cap is then placed through the tube to lock the fixation element to the screws. As demonstrated in the prior art, such tubes attach rigidly to the screw body and do not permit the rotation of the screw body needed to perform locking of the fixation element to the screws.

Recently, there has been the development of capless spinal screws which utilize rotation of the screw body to achieve locking of the fixation element to the capless screws. Current retraction tubes are not capable of being used with capless screws. Since capless screws require rotation of the screw body in order to perform rod locking, an improved retraction tube is needed which allows for rotational screw locking to take place within the tube.

SUMMARY OF THE INVENTION

One object of the invention is to provide a retractor for retracting tissue and that is adapted to rotate or permit rotation of a capped or capless polyaxial screw.

Another object of the invention is to provide a reducer for moving the rod in the retractor.

In one aspect, one embodiment comprises a retractor comprising an elongated member for detachably mounting onto a receiver having a rod receiving channel for receiving a rod, the elongated member comprising an elongated member rod-receiving channel for receiving the rod and for guiding the rod into the receiver rod receiving channel of the receiver after the elongated member is mounted on the receiver and the elongated member rod-receiving channel of the elongated member is generally aligned with the receiver rod-receiving channel of the receiver, the elongated member having a first end for receiving and detachably mounting onto the receiver so that the rod may be received in the elongated member rod-receiving channel of the elongated member while at least a portion of the elongated member substantially simultaneously retracts tissue.

In another aspect, another embodiment comprises a reducer for rotatably mounting on a retractor having an elongated member having a rod-receiving channel, the reducer comprising an elongated tubular member having a reducer channel, the elongated tubular member for mounting on the retractor, the reducer channel and the rod-receiving channel of the elongated member receiving a rod and cooperating to cause the rod to move in the rod-receiving channel of the elongated member and into a receiver channel of a receiver.

In still another aspect, another embodiment comprises an implant system comprising an assembly comprising a receiver having a receiver channel for receiving a rod, a screw for mounting in the receiver, at least one inner member for mounting in the receiver, the receiver, the screw and the at least one inner member cooperating to lock the rod in the receiver channel of the receiver and a retractor comprising a retractor body for detachably mounting onto the receiver; the retractor body comprising a rod-receiving channel for receiving the rod and for guiding the rod into the receiver channel of the receiver, the retractor body having a first end for receiving and detachably mounting to the receiver so that the receiver channel of the receiver can receive the rod while at least a portion of the retractor body substantially simultaneously retracts tissue.

These and other objects and advantages of the invention will be apparent from the following description, the accompanying drawings and the appended claims.

DETAILED DESCRIPTION OF THE ACCOMPANYING DRAWINGS

FIG. 4 is a view of the retraction device or apparatus;

FIG. 5 is a sectional view of the retraction device or apparatus, taken along line 5-5 of FIG. 4;

FIG. 6 is a fragmentary view, partly in cross-section, of a retraction device or apparatus with a capless screw engaged;

FIG. 7 is a fragmentary view of a retraction device or apparatus with a capless screw engaged;

FIG. 8 is a fragmentary view, similar to FIG. 7, showing another position thereof;

FIG. 11 is a fragmentary view of the retraction device or apparatus and capless screw rigidly fixed and showing a rod in a first position;

FIG. 12 is a view similar to FIG. 11 with the rod moved to another position;

FIG. 13 is an enlarged fragmentary view showing the retraction device or apparatus and screw with a locking interface so that rotation of the tube in turn causes rotation of the receiver into a locking position;

FIG. 14 is a perspective view of another embodiment showing a retractor and a reducer;

FIGS. 15-17 are various views illustrating the reducer urging or forcing the rod into a rod-locking channel of the receiver;

FIG. 18 is a view illustrating the reducer being removed from the retractor;

FIG. 19 is a view illustrating the retractor rotating the receiver after the rod is received in the rod-locking channel and the reducer has been removed from the retractor;

FIG. 20 is a sectional view taken along the lines 20-20 in FIG. 17; and

FIG. 21 is an exploded view showing reducer that fits inside the retractor.

DETAILED DESCRIPTION OF THE PREFERRED EMBODIMENTS

Figure 1:
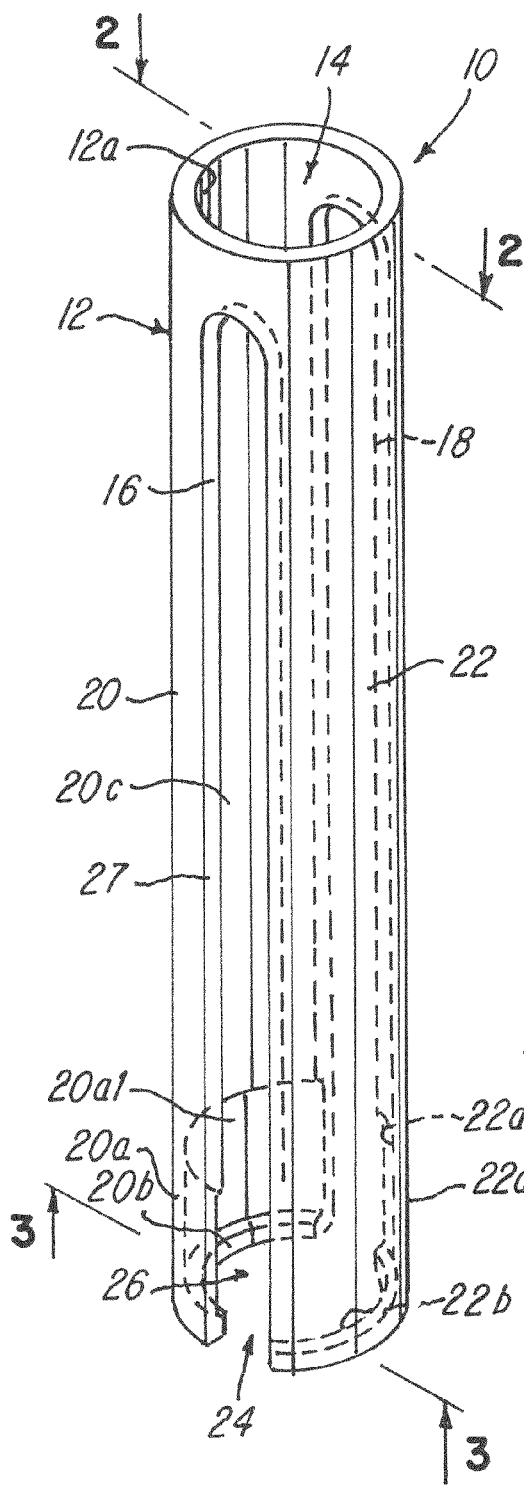
FIG. 1 is perspective view of a retraction device or apparatus according to one embodiment of the invention.
Figure 2:
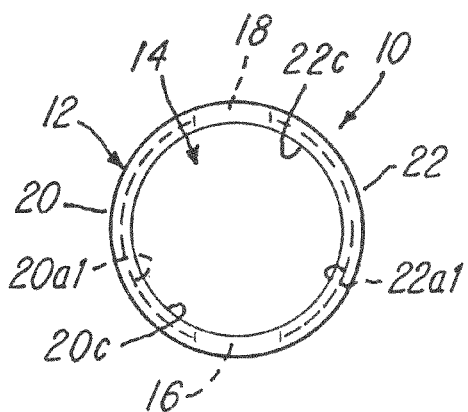
FIG. 2 is a sectional view of a retraction device or apparatus, taken along line 2-2 of FIG. 1.
Figure 3:
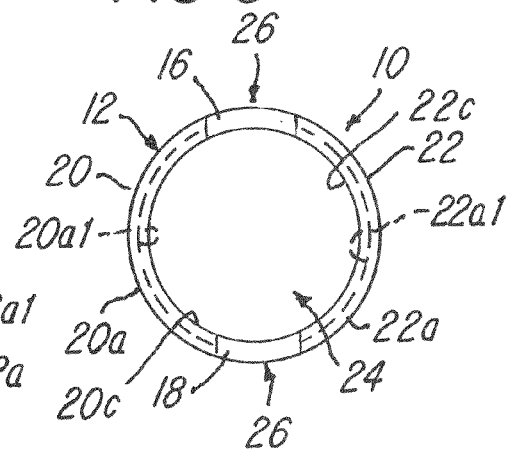
FIG. 3 is a sectional view taken along line 3-3 of FIG. 1.

Referring now to FIGS. 1-21, a retraction tube system is shown comprising a retractor, retraction device or apparatus 10. A first illustrative embodiment is shown relative to FIGS. 1-8 wherein a retractor, retraction device or apparatus 10 is shown. As illustrated in FIG. 1, the retractor, retraction device or apparatus 10 comprises a generally tubular or cylindrical body 12 having an inner wall 12a that defines an aperture 14. The retractor, retraction device or apparatus 10 in the illustration being shown is tubular and cylindrical in cross section. A pair of cut-outs 16 and 18 is provided in the body 12. The cut-outs 16 and 18 define a first elongated portion, leg or wall 20 and a second elongated portion, leg or wall 22 as shown. The cut-outs 16 and 18 also cooperate to define a rod-receiving channel 26 for receiving a rod 28.

Figure 9:
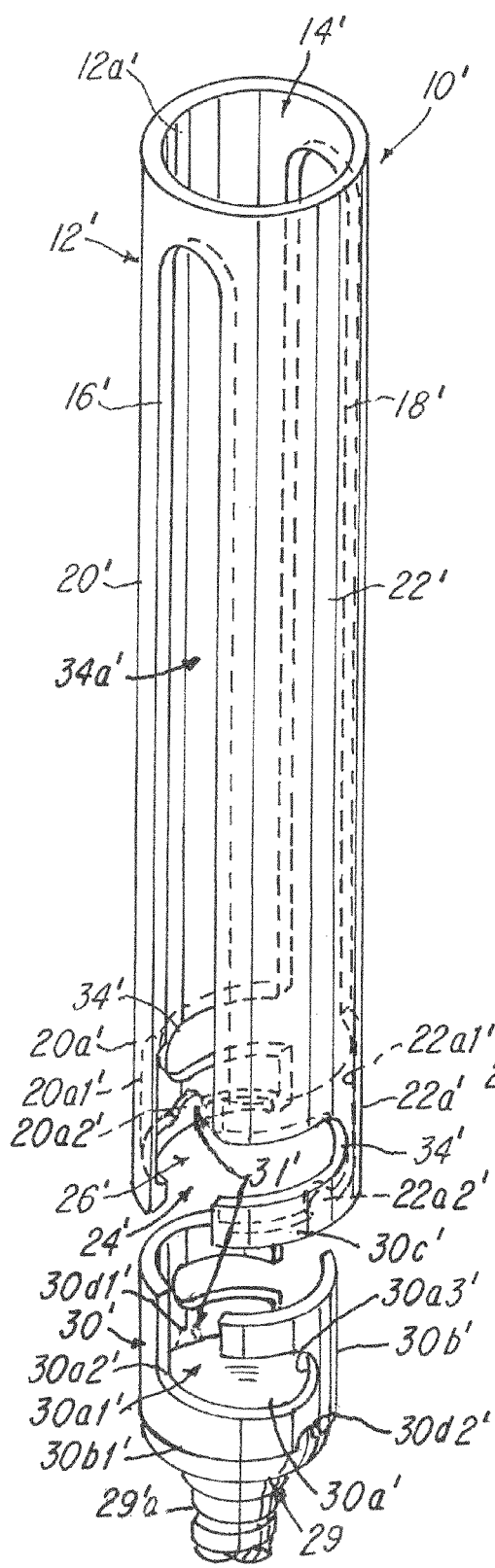
FIG. 9 is an exploded view of another embodiment of a retraction device or apparatus.

Note that an end 20a (FIG. 1) of the first elongated portion 20 has an inner wall 20c (FIG. 2) having a recessed wall 20a1, and an end 22a of the second elongated portion 22 has an inner wall 22c (FIG. 2) having a recessed wall 22a1. The recessed walls 20a1 and 22a2 cooperate to define an area 24 for receiving a polyaxial screw 29 (FIGS. 8 and 9). In the illustration being described, the polyaxial screw 29 comprises a capless receiver or polyaxial screw receiver 30 and a screw 29a (FIG. 8) that is received in the capless receiver 30. The polyaxial screw 29 may be of the type as shown and illustrated in U.S. Pub. Patent Application Nos. US20070043357A1 now issued as U.S. Pat. No. 7,717,943; US20070123867A1; US20060155278A1, now issued as U.S. Pat. No. 7,662,172; US20070123862A1, now issued as U.S. Pat. No. 7,604,655; US20080097457A1; US20080071277A1; US20080249576A1; US20070093827A1, now issued as U.S. Pat. No. 7,686,835, all of which are assigned to the same assignee as the present application and which are incorporated herein by reference and made a part hereof. The polyaxial screw 29 may comprise at least one inner member (not shown), such as a compression member (not shown), of the type disclosed in one or more of the cited applications.

Note that the receiver 30 comprises a generally L-shaped rod-locking channel or slot 30a (FIGS. 6-8) conventionally known. The rod-locking channel 30a has an opening 30a1, a seat 30a2, and a seat 30a3 as shown in FIG. 6. The receiver 30 comprises an outer wall 30b that has a diameter that is dimensioned or adapted to permit the receiver 30 to be received in the receiving area 24 and rotate within and relative to the retraction device or apparatus 10 after the receiver 30 is received between the recessed walls 20a1 and 22a1 in the receiving area 24. Note that the outer wall 30b of receiver 30 may comprise a lip or flange 30b1 having a retaining function described later herein.

As best illustrated in FIGS. 1 and 7, notice that the retractor body 12 has the pair of generally opposed walls, legs, portions 20 and 22 (FIG. 1). The walls, legs or portions 20 and 22 are arcuate or curved in cross-section. The recessed walls 20a1 and 22a1 and associated cut-outs 16 and 18 cooperate to define the rod-receiving channel 26 that receives the rod 28 (FIG. 7). The retractor body 12 comprises at least one or a plurality of lips or flanges 20b and 22b integrally formed in walls 20 and 22 and that engage and cooperate with the lip or flange 30b1 on receiver 30 to retain the receiver 30 in the area 24 and on the retractor body 12. In the illustration being described the first and second elongated portions or legs 20 and 22 are resilient and elastic so that they can deflect to receive the receiver 30 when it is received in the area 24 between the inner walls 20a1 and 22a1. In the illustration being described, a friction or interference fit is provided so that the receiver 30 can be slid onto and rotated within the retractor body 12 in the embodiment shown in FIGS. 1-8.

During a surgical procedure, a surgeon makes an incision and the retraction device or apparatus 10, which has an assembly of the receiver 30 and screw 29a after the screw 29a is received in the receiver 30 and the receiver 30 is received in the receiving area 24, is inserted through the incision and the screw 29a is screwed into bone with a screw driver (not shown) inserted through the aperture 14 of retractor body 12. The retractor, retraction device or apparatus 10 causes the tissue to be retracted during the act of the placement of the polyaxial screw 29.

It should be understood that after the screw 29a is placed and screwed into the bone of the patient, a tool 32 (FIG. 7) may be inserted into the aperture 14 of the retractor body 12 in the illustration of FIGS. 1-8. The tool 32 comprises a working end 32a that is received in the channel or slot 30a of the receiver 30. After the rod 28 has been positioned in the desired position subsequent to screw 29a placement, the tool 32 can be received in the channel or slot 30a and the receiver 30 rotated (clockwise in the illustration being described) in order to lock the receiver 30 onto the rod 28. It should be understood that in the illustration being described the retraction device or apparatus 10 does not rotate during the rotation of the receiver 30.

Moreover, as with the second embodiment described later, it should be understood that the retraction device or apparatus 10 may be mounted onto the receiver 30 and then the screw 29a placed or screwed into the bone, thereby providing a single unit for the surgeon to substantially simultaneously place the screw 29a and retract the tissue. It should be understood that the screw 29a and receiver 30 could alternatively be placed or screwed into the bone and then the retraction device or apparatus 10 placed over and mounted on the receiver 30 if desired.

Note that the retractor body 12 comprises the rod-receiving channel 26 that is generally elongated and traverses a majority or substantially all of the length of the retractor body 12. The rod-receiving channel 26 is aligned with the opening 30a1 of the rod-locking channel 30a so that when a rod 28 is placed in the rod-receiving channel 26 of the retractor body 12 it can be easily aligned with and guided into the opening 30a1 of the rod-locking channel 30a and downward toward the seat 30a2, as illustrated in FIGS. 6 and 7.

After the rod 28 is positioned in the seat 30a2, the tool 32 (FIG. 7) can be used to rotate the receiver 30 to lock the rod 28 in the receiver 30. After the receiver 30 locks the rod 28 therein, the retractor body 12 can be removed and dismounted from the receiver 30 by pulling it away from the receiver 30. In this illustration, the rod-receiving channel 26 in the retractor body 12 is substantially linear or straight, while the rod-locking channel 30a in the receiver 30 is not straight and is generally L-shaped as shown. FIGS. 7 and 8 illustrate the receiver 30 after it has been rotated from the unlocked position (FIG. 7) to the locked position (FIG. 8) using the tool 32.

In the illustrations described herein, the retractor body 12 is tubular and cylindrical, but it should be understood that it could take different forms, such as a solid form, without departing from the scope of the invention. For example, the retractor body 12 could be non-cylindrical (e.g., hexagonal, octagonal, square or like).

In the illustration being described, an indicia 39a (FIG. 8) may be provided on the retractor body 12 and a second indicia 39b provided on the outer wall 30b to facilitate aligning the rod-receiving channel 26 with the opening 30a1 of the rod-locking channel 30a. Alternatively, and as described later herein relative to other embodiments, a coupler 31' (FIG. 9) may be provided that facilitates coupling and aligning the retractor body 12' to the receiver 30'.

Note that a dimension or width (as viewed in FIG. 4) of the rod-receiving channel 26 is substantially the same as a dimension or width of the inlet 30a1 of the rod-locking channel 30a. Advantageously, the channel 26' and retraction body 12' provide an alignment guide for receiving the rod 28' and directing the rod 28' through the slot or channel 26' and into the rod-locking channel 30a' of the receiver 30.

FIGS. 9-13 illustrate another embodiment of the invention. Like parts are identified with the same part numbers in this embodiment, except that an apostrophe ("'") has been added to the part numbers in this embodiment.

In this embodiment, the retraction device or apparatus 10' rotates with the receiver 30' during locking of the rod 28' in the receiver 30'. In this illustration, note that the retraction body 12' of retraction device or apparatus 10' comprises a generally L-shaped rod-receiving channel 34' (FIG. 10) that has a shape and dimension that generally complements a shape and dimension of the rod-locking channel 30a' of the receiver 30'. As best illustrated in FIGS. 11 and 12, the rod 28' is inserted into an elongated portion 34a' of the rod-receiving channel 34' and then moved downward (as viewed) into opening 30a1'. Notice that after the rod 28' is placed in the seat 30a2' of rod-locking channel 30a' of the receiver 30' both the retraction device or apparatus 10' and the receiver 30', are rotated together to the locked position, as illustrated in FIGS. 11 and 12.

After the receiver 30' is locked onto the rod 28, the retraction device or apparatus 10' may be rotated relative to the receiver 30' in a counterclockwise direction in the illustration being described and then removed or detached from the receiver 30'. In this regard, the frictional fit engagement and clamping force between the recessed wall 20a1' and 22a1' and the outer wall 30b' of the receiver 30' is less than the coupling strength between the receiver 30' and the rod 28', thereby permitting the retraction device or apparatus 10' to rotate after the receiver 30' is locked onto the rod 28' and without rotating and unlocking the receiver 30' from the rod 28'.

Figure 10:
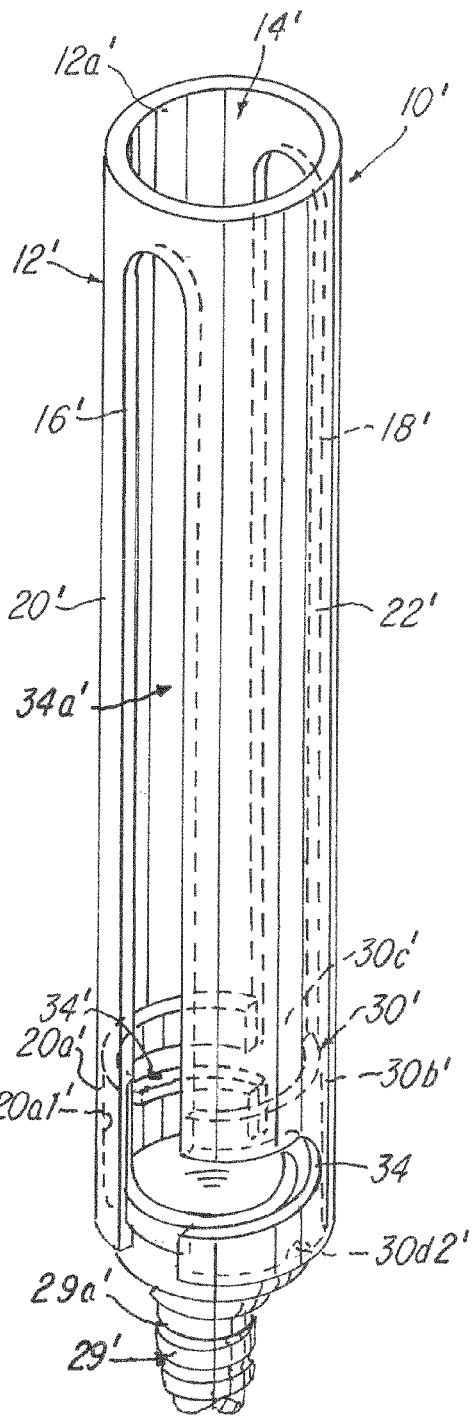
FIG. 10 is a view similar to FIG. 9, showing the retractor mounted on a capless polyaxial screw.

As illustrated in FIGS. 9-11, the receiver 30' may comprise a coupler 31', such as a notch, tooth or other male projections 20a2' and 22a2' that are received in notched areas or slots 30d1' and 30d2', respectfully. This feature facilitates locking the retraction device or apparatus 10' to the receiver 30'. This feature also reduces or facilitates reducing undesired rotation of the retraction device or apparatus 10' relative to the receiver 30' during rotation of the retraction device or apparatus 10' and receiver 30' and locking of the receiver 30' onto the rod 28'. The coupler 31' also facilitates automatic or quick alignment of channel 34' with the rod-locking channel 30a' when the retractor body 12' is mounted on the receiver 30'.

Referring now to FIGS. 14-21, another embodiment of the invention is shown. In this embodiment, like parts are identified with the same part numbers, except that a double apostrophe ("''") mark has been added to the part numbers in FIGS. 14-21. In this embodiment, an implant system is shown comprising a polyaxial screw assembly similar to the assembly shown in FIGS. 6-13. This embodiment further comprises a reducer 60", which will be described later herein. The retractor body 12" is detachably mounted onto the polyaxial screw 29" and receiver or polyaxial screw receiver 30" in the manner describer earlier.

As with the embodiments illustrated in FIGS. 6-13, the retractor body 12" detachably mounts onto the outer wall 30b of the polyaxial screw receiver 30". The retractor body 12" further comprises a rod-receiving channel 34". The rod-receiving channel 34" becomes generally aligned with an opening 30a1" and ultimately to the seat 30a2". As with the prior embodiments, the rod-receiving channel 34" and the retractor body 12" is adapted to facilitate urging and guiding the rod 28" into the channel opening 30a1" and ultimately to the seat 30a2" in the manner described herein.

The retractor body 12" comprises the first elongated portion, leg or wall 20" and the second elongated portion, leg or wall 22" as shown. An end 20a" of the first elongated portion 20" has the inner or recessed wall 20a1", and end 22a" of the second elongated portion 22" comprises the inner or recessed wall 22a1". The recessed walls 20a1" and 22a1" cooperate to define the area 24" for receiving the polyaxial screw receiver 30".

As with prior embodiments, the first and second recessed walls 20a1" and 22a1" of the first and second elongated portions 20" and 22" are dimensioned and adapted to be mounted onto the outer surface 30b" of the polyaxial screw receiver 30". A friction, press or interference fit is provided so that rotating the retractor body 12" will cause the polyaxial screw receiver 30" to rotate as in the embodiment illustrated in FIGS. 9-13. This rotation is performed after the rod 28" has been received in rod-receiving channel 34", guided into and received in the opening 30a1" and seat 30a2" of the rod-locking channel 30a" in order to cause the rod 28" to be received in the locking seat 30a3" of the polyaxial screw receiver 30". As mentioned, the first and second elongated portions or legs 20" and 22" are elastic and resilient and permit the ends 20a" and 22a" to separate to receive the polyaxial screw receiver 30" until it is captured in the receiving area 24". As with the prior embodiment, notice that the polyaxial screw receiver 30" may comprise the edge or lip 30b1". The retractor body 12" comprises the internal lip or flanges 20b" and 22b" that cooperate with the lip 30b1" to retain the retractor body 12" on the polyaxial screw receiver 30".

The at least one inner wall, such as recessed wall 20a1" and recessed wall 22a1", is adapted to frictionally engage the outer surface 30b" so that by rotating the retractor body 12", the receiver 30" will also rotate until the rod 28" becomes locked in the rod-locking channel 30a" of polyaxial screw receiver 30". In another illustrative embodiment, the at least one inner wall, such as inner wall 20a1" and inner wall 22a1", are mounted on the polyaxial screw receiver 30" and are adapted to permit the polyaxial screw receiver 30" to be rotated to lock the rod 28" in the polyaxial screw receiver 30" while the retractor body 12" is held stationary as in the embodiment of FIGS. 1-8. In that application, the retractor body 12" is held stationary while a tool, such as the tool 32" in FIG. 7, is used to rotate the retractor body 12" to the locked position whereupon the rod 28" becomes locked in the polyaxial screw receiver 30".

As with the embodiment illustrated in FIGS. 9-13, the rod-receiving channel 34" comprises a shape, configuration and/or dimension that is generally the same as the shape, configuration or dimension of the rod-locking channel 30a" so that when the retractor body 12" is mounted on the polyaxial screw receiver 30", the rod-receiving channel 34" and rod-locking channel 30a" become generally aligned. It should be understood that, as with the prior embodiments, the receiving area 24" generally defines a female receiving area that generally complements the shape of the outer surface of the polyaxial screw receiver 30". This alignment enables the retractor body 12" to be rotated in a first direction, such as in a clockwise direction, to cause the polyaxial screw receiver 30" to rotate and lock the rod 28" in the polyaxial screw receiver 30" after the rod 28" has been moved through the rod-receiving channel 34" and into the rod-locking channel 30a". Thereafter, the retractor body 12" may be rotated in a second direction, which is generally opposite the first direction, after the polyaxial screw receiver 30" is locked onto the rod 28" and without rotating the polyaxial screw receiver 30" in the second direction as mentioned earlier. In this regard, after the rod 28" has become locked in the polyaxial screw receiver 30", the retractor body 12" can be rotated so as to align the rod-receiving channel 34" with the rod 28" so that the retractor body 12" can be moved axially (in the direction of arrow A in FIG. 18) away from the polyaxial screw receiver 30" and dismounted therefrom.

The retractor body 12" is fit or mounted onto the polyaxial screw receiver 30" with a friction, press or interference fit. As mentioned earlier, the frictional engagement and gripping strength between the first and second inner walls 20a1" and 22a1" and the outer surface 30b" of the polyaxial screw receiver 30" is less than a frictional engagement and coupling strength between the polyaxial screw receiver 30" and the rod 28". This permits the retractor body 12" to rotate (counter-clockwise in the illustration) about the outer wall or surface 30b" after the polyaxial screw receiver 30" is locked onto the rod 28" and without unlocking or rotating the polyaxial screw receiver 30" to the unlock position.

As illustrated in FIG. 14, the rod-receiving channel 34" is generally L-shaped like the embodiment of FIGS. 11-13. A portion 34a" (FIG. 14) traverses a substantial or majority of a length of the retractor body 12". It should be understood, however, that the retractor body 12" of the type illustrated in FIGS. 1-20 could also be used with this embodiment and comprise a channel, like the channel 26" that is substantially straight or linear, that traverses a majority of a length of the retractor body 12". Thus, the rod-receiving channel 34" could be entirely straight or linear even though the rod-locking channel 30a" is not entirely straight. Alternatively, both the rod-locking channel 30a" and the rod-receiving channel 34" could be either linear or non-linear as illustrated in the figures.

As with the embodiment shown in FIGS. 11-13, the retractor system 10" may comprise the coupler 31" for facilitating coupling and securing the retractor body 12" onto the receiver 30". In the illustration described, the coupler 31" may comprise the at least one or a plurality of projection 20a2" and 22a2" in the walls 20" and 22" of the retractor body 12". As described earlier herein, the projections 20a2" and 22a2" mate with and are received in the notched-out areas 30d1" and 30d2" in receiver 30". The notched-out areas 30d1" and 30d2" each have a shape that generally complements the shape of the projections 20a2" and 22a2".

As with the embodiment illustrated in FIG. 10, for example, the coupler 31" facilitates securing the retractor body 12" to the receiver 30" and causing the rod-locking channel 30a" and rod-receiving channel 34" to become generally aligned. If a coupler 31" is not provided, the indicia or marking 39a, 39b (FIG. 8) or other means for aligning the rod-receiving channel 34" with the opening 30a1" of the rod-locking channel 30a" may be provided.

As with the prior embodiments, the retractor body 12" is generally tubular and comprises the first wall 20" and the second wall 22" that are defined by the cut-out areas 16" and 18. The cut-out areas 16" and 18" cooperate to define the rod-receiving channel 34" as with the prior illustrative embodiment.

As with prior embodiments, the retractor body 12" is sized and adapted to permit a tool, such as the tool 32" (FIG. 7), to be placed in the area 14" in order to either rotatably drive the receiver 30" or to engage the head (not shown) of the screw 29a" in order to screw the screw 29a" into bone during the surgical procedure.

One feature of the embodiment shown in FIGS. 14-21 is the use of a reducer 60" for urging or driving the rod 28" in the rod-receiving channel 34" until it is received in the opening 30a1" and seats 30a2", 30a3" of the rod-locking channel 30a". The reducer 50" comprises a non-linear reducer channel 66" which in the embodiment illustrated in FIGS. 14-21 is helical. Note in the illustration being described that reducer 60" comprises a tubular wall 61" having a first cut-out 62" and a second cut-out 64" which cooperate to define the reducer channel 66". The rod 28" may be placed through the cut outs 62" and 64" as illustrated in FIG. 14 and into the reducer channel 66". In the illustration being described, the first and second cut-out areas 62" and 64" define wall portions 61a" and 61b" that are helical. The cut outs 62" and 64" and wall portions 61a" and 61b" and are spaced approximately 180° apart to define the helical reducer channel 66". An end 61c of the wall 61" comprises a generally circular knob or grip 68" for facilitating gripping the reducer 60". The grip 68" is integrally formed with the tubular wall 61" and capable of rotating the wall 61" upon rotation of the grip 68". The grip 68" also comprises an annular flange 72" that engages and cooperates with a seat 74" in the retractor body 12" so that the reducer 60" may be rotatably mounted onto the retractor body 12". As shown in FIG. 21, another embodiment is provided where the tubular wall 61" is dimensioned and adapted to be received in the area 14" inside the retractor body 12" as shown.

As best illustrated in FIG. 14, the reducer 60" comprises an area 80" that is dimensioned and adapted to receive and permit rotation of the retractor body 12" inside the reducer 60. The rod 28" is placed and traversed through the reducer channel 66" and through the rod-receiving channel 34" as shown. The reducer knob, grip or handle 68" is rotated which causes the rod 28" to traverse the length of both the reducer channel 66" and the rod-receiving channel 34" in the retractor body 12", as illustrated in FIGS. 15-17.

The ends of the tubular wall portions 61a" and 61b" each comprise a stop 82" (FIG. 17) that engages and captures the rod 28" when the rod 28" has reached the end of its travel in the reducer channel 66" and is received in the seat 30a2" of the rod-locking channel 30a", as illustrated in FIGS. 17 and 18. In the illustration, the stop 82" comprises a curved seat 82a" formed or provided at the ends of the wall portions 61a" and 61b". The curved seat 82a" captures and engages the rod 28" as shown in FIG. 17.

After the rod 28" is received in the seat 30a2" of the rod-locking channel 30a" of the receiver 30", the reducer 60" may be removed from the retractor body 12" by moving the reducer 60" axially in the direction of arrow B in FIG. 18. After the reducer 60" has been removed from the retractor body 12", the receiver 30" may be rotated (in a clockwise direction in the illustration being described) to lock the rod 28" in the receiver 30" in the manner described earlier relative to FIGS. 9-13. Alternatively, the retractor body 12" may be rotated by using the tool 32" in the manner illustrated in FIG. 7 relative to the prior embodiment.

In order to stabilize or retain the retractor body 12" in a stationary position during rotation of the reducer 60", a stabilizer 40" (FIGS. 15 and 16) or means for stabilizing the retractor body 12" may be provided. In the illustration being described, the stabilizer 40" may take the form of a plurality of apertures 40a" and 40b" in the retractor body 12" wall. During use, a tool (not shown), such as a screwdriver or other elongated shafted tool or dow, may be placed through the apertures 40a" and 40b" and used to hold the retractor body 12" stationary during rotation of the knob 68" of reducer 60". The tool (not shown) may also be used to rotate the retractor body 12" in order to rotate the receiver 30" to an unlocked or locked position and to pull or detach the retractor body 12" from the receiver 30".

It should be appreciated that a length of the reducer 58" is selected so that when the rod 28" has reached the stops 82" at the ends of the wall portions 61a" and 60b", respectively, the rod 28" is seated at the seat 30a2". This facilitates properly situating and seating the rod 28" in the rod-locking channel 30a" before the receiver 30" is rotated from the open position shown in FIG. 18 to the locked position illustrated in FIG. 19.

In the illustration being described, the retraction device or apparatus 10 is made of stainless steel, but it should be understood that it could be made of any suitable material that is capable of performing the functions described herein. Thus, for example, the retraction device or apparatus 10 could be made of a polymer material, plastic, composite material, metallic material, such as titanium, or other suitable material.

Advantageously, the retractor and reducer systems and methods described herein provide means, system and apparatus for guiding or placing a polyaxial screw in a patient and/or situating a rod in the polyaxial screw, while substantially simultaneously retracting tissue during a surgical procedure.

While the form of apparatus herein and methods described constitutes a preferred embodiment of this invention, it is to be understood that the invention is not limited to this precise form of apparatus, and that changes may be made therein without departing from the scope of the invention.

What is claimed is:

1. A reducer for rotatably mounting on a retractor having an elongated member having an elongated member rod-receiving channel, said reducer comprising:

an elongated tubular member comprising a tubular wall having a first helical cut out area and a second helical cut out area, said first and second helical cut out areas being generally opposed and spaced approximately 180 degrees apart in said elongated tubular member and defining a reducer channel that is helical, said elongated tubular member being adapted to be mounted on the retractor, said reducer channel and said elongated member rod-receiving channel of said elongated member receiving a rod and cooperating to cause said rod to move in said elongated member rod-receiving channel of the elongated member and into a receiver rod-receiving channel of a receiver;

said first helical cut out area and said second helical cut out area guiding said rod in said elongated member rod-receiving channel when said reducer is rotated and urging said rod axially along an axis of said reducer such that an axis of said rod remains generally radial with respect to said axis of said reducer;

said first helical cut out area and said second helical cut out area extending along a longitudinal length of said elongated member to permit said elongated member to rotate greater than 360 degrees during said urging of said rod and rotation of said reducer.

2. The reducer as recited in claim 1 wherein said reducer channel is non-linear.

3. The reducer as recited in claim 1 wherein said reducer comprises a grip for manually rotating said reducer about said elongated member.

4. The reducer as recited in claim 1 wherein said reducer comprises an internal reducer receiving area adapted and dimensioned to receive said elongated member of said retractor so that said reducer can be rotatably mounted on said elongated member.

5. The reducer as recited in claim 1 wherein said reducer being adapted and dimensioned to be rotatably mounted inside said elongated member.

6. The reducer as recited in claim 1 wherein said reducer comprises at least one stop associated with said reducer channel to prevent over rotation of said reducer once the rod is captured in a seat of said receiver channel of said receiver.

7. The reducer as recited in claim 1 in combination with said retractor, said retractor further comprising:

said elongated member for detachably mounting onto said receiver having a receiver rod-receiving channel for receiving said rod;

said elongated member comprising an elongated member rod-receiving channel for receiving said rod and for guiding said rod into said receiver rod-receiving channel of said receiver after said elongated member is mounted on said receiver and said elongated member rod-receiving channel of said elongated member is generally aligned with said receiver rod-receiving channel of the receiver;

said elongated member having a first end for receiving and detachably mounting onto said receiver so that said rod may be received in said elongated member rod-receiving channel of said elongated member while at least a portion of said elongated member substantially simultaneously retracts tissue.

8. The reducer in combination with said retractor as recited in claim 7 wherein said elongated member comprises:

at least one inner wall for mounting onto an outer surface of said receiver, said at least one inner wall being adapted to permit said receiver to be rotated by rotating said elongated member until said rod becomes locked in said receiver.

9. The reducer in combination with said retractor as recited in claim 7 wherein said elongated member comprises:

at least one inner wall for mounting onto an outer surface of said receiver, said at least one inner wall being adapted to permit said receiver to receive said rod in said receiver while said elongated member is held stationary.

10. The reducer in combination with the retractor as recited in claim 9 wherein a cap is screwed onto said receiver to lock said rod in said receiver.

11. The reducer in combination with said retractor as recited in claim 7 wherein said elongated member is adapted to permit said elongated member to be removed from said receiver by moving said elongated member axially away from said receiver after said rod is locked in said receiver.

12. The reducer in combination with said retractor as recited in claim 7 wherein at least a portion of said rod-receiving channel comprises a shape or configuration that is generally the same as a shape or configuration of said receiver rod-receiving channel so that when said elongated member is mounted onto said receiver, said rod-receiving channel and said receiver rod-receiving channel can become generally aligned to permit said rod to be received so that said elongated member can be rotated in a first direction to cause said receiver to lock said rod in said receiver and then rotated in a second direction generally opposite said first direction without unlocking said rod from said receiver.

13. The reducer in combination with said retractor as recited in claim 7 wherein said elongated member comprises an end having a first recessed wall and a second recessed wall that generally opposes said first recessed wall, said first and second recessed walls defining a first shape that generally complements a second shape of an outer surface of said receiver.

14. The reducer in combination with said retractor as recited in claim 13 wherein said first and second shapes are arcuate and dimensioned to enable said end of said elongated member to be fit onto said receiver with a press or interference fit.

15. The reducer in combination with said retractor as recited in claim 13 wherein a frictional engagement between said first and second recessed walls and said outer surface is less than a coupling strength between the receiver and said rod, thereby permitting said elongated member to rotate after the receiver is locked onto the rod and without unlocking the said receiver from the rod.

16. The reducer in combination with said retractor as recited in claim 7 wherein said elongated member is adapted to permit said elongated member to be removed from said receiver by moving said elongated member axially away from said receiver after said rod is locked in said receiver.

17. The reducer in combination with said retractor as recited in claim 7 wherein said rod-receiving channel elongated member traverses a majority of a longitudinal length of said elongated member.

18. The reducer in combination with said retractor as recited in claim 7 wherein said receiver rod-receiving channel in said receiver is not entirely straight and said elongated member rod-receiving channel is generally straight.

19. The reducer in combination with said retractor as recited in claim 7 wherein neither of said receiver rod-receiving channel in said receiver nor said elongated member rod-receiving channel is straight.

20. The retractor-reducer in combination with said retractor as recited in claim 7 wherein said elongated member comprises a first end having a recessed area adapted to capture said receiver with a frictional engagement that permits said receiver to be rotated by said elongated member and permit said elongated member to rotate or move independent of any movement of said receiver.

21. The reducer in combination with said retractor as recited in claim 7 wherein said first end comprises a coupler or aligner for facilitating coupling or aligning, respectively, said elongated member to said receiver.

22. The reducer in combination with said retractor as recited in claim 21 wherein said coupler comprises at least one projection on at least one of said elongated member or said receiver and a generally complementary receiving area on the other of said receiver or said at least one of said elongated member, respectively, for receiving said at least one projection to facilitate coupling said elongated member to said receiver.

23. The reducer in combination with said retractor as recited in claim 22 wherein said coupler or aligner causes said receiver rod-receiving channel of said receiver and said elongated member rod-receiving channel to become generally aligned when said elongated member is mounted onto said receiver.

24. The reducer in combination with said retractor as recited in claim 7 wherein said elongated member is generally tubular and comprises a first arcuate wall and a second arcuate wall generally opposing said first arcuate wall, said first and second arcuate walls having ends that are spaced to define said rod-receiving channel, said elongated member is sized to permit a tool to be used to screw said screw in said receiver and after said elongated member is mounted onto said receiver.

25. The reducer in combination with said retractor as recited in claim 7 wherein said elongated member comprises a first end for mounting onto said receiver and a second end opposite said first end, said second end having a stabilizer for holding said elongated member.

26. The reducer in combination with said retractor as recited in claim 7 wherein said receiver is a capless receiver.

27. The reducer in combination with the retractor as recited in claim 7 wherein at least a portion of said rod-receiving channel of said retractor body comprises a shape or configuration that is generally the same as said shape or configuration of said receiver rod-receiving channel of said receiver so that when said elongated member is mounted onto said receiver, said rod can be guided from said rod-receiving channel of said retractor body to said receiver rod-receiving channel of said receiver.

28. The reducer in combination with the retractor as recited in claim 7 wherein said elongated member rod-receiving channel of said elongated member and said reducer channel are adapted to receive said rod and cooperate to guide and urge said rod into said receiver channel upon rotation of the reducer;
   wherein after said rod is received in said receiver, said receiver is adapted to be rotated by said retractor to lock said rod in said receiver.

29. The reducer as recited in claim 1, in combination with an implant system, said implant system further comprising:
   an assembly; said assembly comprising:
      said receiver having said receiver channel for receiving a rod;
      a screw for mounting in said receiver;
      at least one inner member for mounting in the receiver; said receiver, said screw and said at least one inner member cooperating to lock said rod in said receiver channel of said receiver; and
   said retractor comprising:
      a retractor body for detachably mounting onto said receiver; said retractor body comprising said elongated member rod-receiving channel for receiving said rod and for guiding said rod into said receiver channel of said receiver;
      said retractor body having a first end for receiving and detachably mounting to said receiver so that said receiver channel of said receiver can receive said rod while at least a portion of said retractor body substantially simultaneously retracts tissue.

30. The reducer in combination with an implant system as recited in claim 29 wherein said retractor body further comprises:
   at least one inner wall for mounting onto an outer surface of said receiver, said at least one inner wall being adapted to cause said receiver to rotate by rotating said retractor body until said rod becomes locked in said receiver.

31. The reducer in combination with an implant system as recited in claim 29 wherein said retractor body comprises:
   at least one inner wall for mounting onto an outer surface of said receiver, said at least one inner wall being adapted to permit said receiver to be rotated to lock said rod in said receiver while said retractor body is held stationary.

32. The reducer in combination with an implant system as recited in claim 29 wherein said retractor body is adapted to permit said retractor body to be removed from said receiver by moving said retractor body axially away from said receiver after said receiver has been rotated.

33. The reducer in combination with an implant system as recited in claim 29 wherein at least a portion of said rod-receiving channel comprises a shape or configuration that is generally the same as a shape or configuration of said receiver channel of said receiver so that when said retractor body is mounted onto said receiver, said rod-receiving channel and said receiver channel of said receiver becomes generally aligned to enable said retractor body to be rotated in a first direction to cause said receiver to rotate and lock said rod in said receiver channel of said receiver and then rotated in a second direction generally opposite said first direction without rotating said receiver in said second direction.

34. The reducer in combination with an implant system as recited in claim 33 wherein said retractor body comprises an end having a first recessed wall and a second recessed wall that generally opposes said first recessed wall, said first and second recessed walls cooperating to define a female receiving area that generally complements and mates with an outer surface of said receiver.

35. The reducer in combination with an implant system as recited in claim 34 wherein said end of said retractor body fits onto said receiver with a press or interference fit.

36. The reducer in combination with an implant system as recited in claim 34 wherein a frictional engagement between said first and second recessed walls and said outer surface is less than a coupling strength between the receiver and said rod, thereby permitting said retractor body to rotate or slidably move off said receiver after the receiver is locked onto the rod without unlocking the receiver from the rod.

37. The reducer in combination with an implant system as recited in claim 29 wherein said retractor body is adapted to permit said retractor body to be removed from said receiver by moving said retractor body axially away from said receiver after said rod is locked in said receiver.

38. The reducer in combination with an implant system as recited in claim 29 wherein said rod-receiving channel of said retractor body traverses a majority of a longitudinal length of said retractor body.

39. The reducer in combination with an implant system as recited in claim 29 wherein said receiver channel of said receiver is not entirely straight and said rod-receiving channel of said retractor body is generally straight.

40. The reducer in combination with an implant system as recited in claim 29 wherein neither said receiver channel of said receiver nor said rod-receiving channel of said retractor body are straight.

41. The reducer in combination with an implant system as recited in claim 29 wherein said retractor body comprises a first end having a recessed area adapted to capture said receiver with a frictional engagement that permits said receiver to be rotated by said retractor body and permit said retractor body to rotate, slide off of said receiver, or move independent of any movement of said receiver.

42. The reducer in combination with an implant system as recited in claim 29 wherein said first end comprises a coupler or aligner for facilitating coupling or aligning, respectively, said retractor body to said receiver.

43. The reducer in combination with an implant system as recited in claim 42 wherein said coupler or aligner comprises at least one projection on at least one of said retractor body or said receiver and a generally complementary receiving area on the other of said receiver or said at least one of said retractor body, respectively, for receiving said at least one projection to facilitate coupling said retractor body to said receiver.

44. The reducer in combination with an implant system as recited in claim 43 wherein said coupler or aligner causes said receiver channel of said receiver and said rod-receiving channel of said retractor body becomes generally aligned when said retractor body is mounted onto said receiver.

45. The reducer in combination with an implant system as recited in claim 29 wherein said retractor body is generally tubular and comprises a first arcuate wall and a second arcuate wall generally opposing said first arcuate wall, said first and second arcuate walls having ends that are spaced to define said rod-receiving channel of said retractor body, said retractor body is sized to permit a tool to be used to screw said screw after said retractor body is mounted onto said receiver.

46. The reducer in combination with an implant system as recited in claim 29 wherein said retractor body comprises a first end for mounting onto said receiver and a second end opposite said first end, said second end having a stabilizer for holding said retractor body.

47. The reducer in combination with an implant system as recited in claim 29 wherein said at least one inner member is a cap.

48. The reducer in combination with an implant system as recited in claim 29 wherein said screw is a polyaxial screw.

49. The reducer in combination with an implant system as recited in claim 29 wherein said screw receiver is a polyaxial screw receiver.

50. The reducer in combination with an implant system as recited in claim 29 wherein said receiver is a capped receiver.

51. The reducer in combination with an implant system as recited in claim 29 wherein said receiver is a capless receiver.

52. The reducer in combination with an implant system as recited in claim 29 wherein said channel of said receiver is generally L-shaped.

* * * * *

UNITED STATES PATENT AND TRADEMARK OFFICE
CERTIFICATE OF CORRECTION

| | | |
|---|---|---|
| PATENT NO. | : 8,142,436 B2 | Page 1 of 1 |
| APPLICATION NO. | : 12/477489 | |
| DATED | : March 27, 2012 | |
| INVENTOR(S) | : David Louis Kirschman | |

It is certified that error appears in the above-identified patent and that said Letters Patent is hereby corrected as shown below:

In the specification

In Column 3, Line 32, please delete "22a2" and insert -- 22a1 -- therefor.

In Column 3, Line 42, after US20080097457A1;, please insert -- now issued as U.S. Pat. No. 8,012,185; --.

In Column 3, Line 42, after US20080071277A1;, please insert -- now issued as U.S. Pat. No. 8,092,504; --.

In Column 3, Line 43, after US20080249576A1;, please insert -- now issued as U.S. Pat. No. 8,097,025; --.

In Column 8, Line 4, please delete "18" and insert -- 18" -- therefor.

In Column 8, Line 28, after 61b" please delete "and".

In Column 8, Line 43, please delete "60", and insert -- 60" -- therefor.

In the claims

In Column 11, Line 41, Claim 20, after The, please delete "retractor".

Signed and Sealed this
First Day of December, 2015

Michelle K. Lee
*Director of the United States Patent and Trademark Office*